United States Patent
Biedermann

(10) Patent No.: US 10,052,142 B2
(45) Date of Patent: Aug. 21, 2018

(54) BONE PLATE WITH ENLARGED ANGLE OF INCLINATION FOR A BONE ANCHOR TO A FAVORED SIDE

(71) Applicant: BIEDERMANN TECHNOLOGIES GMBH & CO. KG, Donaueschingen (DE)

(72) Inventor: Markku Biedermann, Miami, FL (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 492 days.

(21) Appl. No.: 14/688,970

(22) Filed: Apr. 16, 2015

(65) Prior Publication Data

US 2015/0320462 A1 Nov. 12, 2015

Related U.S. Application Data

(60) Provisional application No. 61/981,058, filed on Apr. 17, 2014.

(51) Int. Cl.
*A61B 17/80* (2006.01)

(52) U.S. Cl.
CPC ...... *A61B 17/8057* (2013.01); *A61B 17/8014* (2013.01); *A61B 17/8033* (2013.01); *A61B 17/8047* (2013.01); *A61B 17/8052* (2013.01)

(58) Field of Classification Search
CPC ........................... A61B 17/80–17/8095
See application file for complete search history.

(56) References Cited

U.S. PATENT DOCUMENTS 6,139,550 A * 10/2000 Michelson ......... A61B 17/1604
606/287
6,322,562 B1 * 11/2001 Wolter .................. A61B 17/72
606/287

(Continued)

FOREIGN PATENT DOCUMENTS

CN 201692038 U 1/2011
JP 10-501444 2/1998

(Continued)

OTHER PUBLICATIONS

Lorich, et al., "Dynamic Compression Principle", AO Surgery Reference, https://www2.aofoundation.org/wps/portal/lut/p/cl/04_SBK8xLLM9MSSzPy8xBZ9 . . . Aug-01-2014 (taken from Ruedi TP Buckley R, Moran GC (2007) *AO Principles of Fracture Management*. 2nd ed vol. 1. Stutgart New York: ThiemeVerlag) (2 pgs.).

(Continued)

*Primary Examiner* — Zade Coley
(74) *Attorney, Agent, or Firm* — Gordon & Jacobson, P.C.

(57) ABSTRACT

The invention relates to a bone plate assembly for use in orthopedic or trauma surgery. The bone plate assembly includes a plate member having a top side and a bottom side at least one passage extending from the top side to the bottom side; wherein the at least one passage includes a first bore with a first end open towards the top side and a second end, a seat portion configured to receive the head of the bone anchor; and wherein the first bore comprises a first central axis and the seat portion comprises a second central axis, and wherein the first central axis and the second central axis intersect each other within the passage; and a second bore open towards the bottom side.

39 Claims, 4 Drawing Sheets

(56) References Cited

U.S. PATENT DOCUMENTS

| | | | | |
|---|---|---|---|---|
| 6,623,486 | B1* | 9/2003 | Weaver | A61B 17/8057 606/281 |
| 7,033,394 | B2* | 4/2006 | Michelson | A61B 17/7059 623/17.11 |
| 7,951,178 | B2* | 5/2011 | Jensen | A61B 17/8057 606/291 |
| 8,142,485 | B2* | 3/2012 | Buhren | A61B 17/8033 606/289 |
| 8,277,493 | B2* | 10/2012 | Farris | A61B 17/7059 606/286 |
| 8,323,543 | B2* | 12/2012 | Michelson | A61B 17/8605 264/162 |
| 8,343,196 | B2 | 1/2013 | Schneider | |
| 8,409,260 | B2* | 4/2013 | Biedermann | A61B 17/7032 606/301 |
| 8,632,545 | B2* | 1/2014 | Sarangapani | A61B 17/1728 606/280 |
| 8,740,955 | B2* | 6/2014 | Bottlang | A61B 17/8042 606/286 |
| 8,808,335 | B2* | 8/2014 | Biedermann | A61B 17/8042 411/403 |
| 2002/0016595 | A1* | 2/2002 | Michelson | A61B 17/8605 606/301 |
| 2002/0022843 | A1* | 2/2002 | Michelson | A61B 17/8605 606/70 |
| 2006/0264946 | A1* | 11/2006 | Young | A61B 17/1728 606/915 |
| 2007/0043366 | A1* | 2/2007 | Pfefferle | A61B 17/8052 606/279 |
| 2007/0055249 | A1* | 3/2007 | Jensen | A61B 17/1655 606/288 |
| 2008/0051786 | A1* | 2/2008 | Jensen | A61B 17/8057 606/86 A |
| 2008/0249573 | A1* | 10/2008 | Buhren | A61B 17/8033 606/286 |
| 2012/0059425 | A1* | 3/2012 | Biedermann | A61B 17/8042 606/291 |
| 2012/0203348 | A1* | 8/2012 | Michelson | A61B 17/7059 623/17.16 |

FOREIGN PATENT DOCUMENTS

| | | |
|---|---|---|
| JP | 2001-525702 | 12/2001 |
| WO | WO 01/26566 A1 | 4/2001 |
| WO | WO 2009/063489 A2 | 5/2009 |

OTHER PUBLICATIONS

Extended European Search Report for corresponding European Application No. 14200086.8-1506, European Search Report dated Mar. 24, 2015 and dated Apr. 2, 2015, (6pgs.).

* cited by examiner

BONE PLATE WITH ENLARGED ANGLE OF INCLINATION FOR A BONE ANCHOR TO A FAVORED SIDE

CROSS-REFERENCE TO RELATED APPLICATION

This application claims the benefit of U.S. Provisional Patent Application Ser. No. 61/981,058, filed on Apr. 17, 2014, the entire content of which is hereby incorporated by reference.

BACKGROUND

The invention relates to a bone plate assembly for the immobilization of bones or bone fragments. Particularly, the invention relates to a bone plate assembly comprising a bone plate and a bone anchor, the bone plate assembly allowing an enlarged angle of inclination to one side for the bone anchor with respect to a vertical axis through the plate at a position of a bone anchor hole.

US 2012/0059425 A describes a bone plate assembly with a polyaxial coupling between the bone anchors of the bone plate assembly and the plate member with an increased range of angular motion and a low profile.

Lorich D G and Gardner M J describe a limited-contact dynamic compression plate assembly with elongated holes allowing 25° inclination of a bone anchor in the longitudinal plane, and up to 7° inclination in the transversal plane (Ruedi T P, Buckley R, Moran C G (2007) *AO Principles of Fracture Management.* 2nd ed. Vol. 1. Stuttgart New York: Thieme-Verlag).

In the field of spinal surgery, U.S. Pat. No. 8,409,260 B2 describes a bone fixation assembly with a bone anchor and a receiving part allowing an enlarged pivot angle of the bone anchor to one side.

While the known bone plate assemblies can provide polyaxial adjustment of the bone screws relative to the bone plate with an equal angle of inclination to each side, there is still a need for an improved bone plate assembly which allows for an increased angle of inclination with respect to a vertical axis through the plate at a position of a bone anchor hole to a favored side, while still providing a low profile of the plate-screw construct as well as high stability. For example, there might be anatomical situations where the angle of inclination relative to a vertical axis through the plate at a position of a bone anchor hole should be increased to only one side. This may be the case, for example, in the context of fractures of the hand or the shoulder.

SUMMARY

According to an aspect of embodiments of the present invention, a bone plate assembly allows a polyaxial adjustment of the bone anchor and the plate with an enlarged angle of inclination to one side, while simultaneously providing a low profile in terms of a low thickness and a high angular stability.

Aspects and features of embodiments of the present invention are described herein with respect to some exemplary embodiments and are set forth in the claims.

A bone plate assembly according to one or more embodiments of the present invention comprises a seat for the bone anchor, the central axis of which is inclined with respect to a vertical axis through the plate at a position of the bone anchor hole. The seat is configured to allow insertion of the bone anchor up to around 20° with respect to the Zero-position of the bone anchor in the seat corresponding to a total range of motion of up to at least 40°. Due to the design of the holes in the plate, particularly the inclined position of the seat for the bone anchor, the motion cone is tilted so as to provide an increased angulation to a favored side. Hence, e.g. an increased insertion angle of 30° to one side can be reached.

In certain anatomical situations the plate member might be angled, for example a distal radius plate in hand surgery. In this event, the present invention provides an enlarged angle of inclination in the favored direction of the angled portion of the plate member without increasing the thickness of the plate. Moreover, in case of a locking bone plate, a thread axis of the thread for the locking screw can be provided perpendicular to the surface of the bone plate. Therefore, conical threaded holes or inclined threaded holes may be avoided.

The number of holes as well as their design defining the desired side of the enlarged angle of inclination can be adapted to the anatomical requirements easily, thus providing a high variety of applications.

The bone anchor may be fixed relative to the plate by a locking element. With the locking element, the angular stability of the bone anchor may be increased and the bone anchor may be secured against pull-out. Different locking elements can be provided to achieve either full locking or frictional locking or to allow free angulation while only preventing pull-out of the bone anchor. Besides its application as a locking plate of the bone plate assembly according to the invention, the plate assembly can also be used without a locking element, i.e. as a non-locking plate.

The bone plate assembly according to the invention may have one hole or more than one hole, i.e. a plurality of holes dependent on the clinical application. Furthermore, the plate member may have offset holes which are offset from a central longitudinal line for more variety of usage. The plate member can be designed to have a minimal bone contact area and can be used as a dynamic plate. Also, the plate member may be contoured to provide a specific shape for specific clinical applications.

The bone plate assembly is suitable for various clinical applications. For example, the bone plate assembly is suitable for applications in areas including bones or bone parts, where an increased angle between the bone plate and the bone anchor is advantageous so as to best adapt to the anatomical situation, for example in the context of fractures of the hand or the shoulder. The design of the holes leads to a low profile of the whole bone plate assembly rendering it suitable for the application in areas with minimum soft tissue coverage such as in the case of the hand or the pelvis.

BRIEF DESCRIPTION OF THE DRAWINGS

Further features and advantages of the present invention will become apparent from the description of some embodiments with reference to the accompanying drawings. In the drawings.

DETAILED DESCRIPTION

Figure 1:
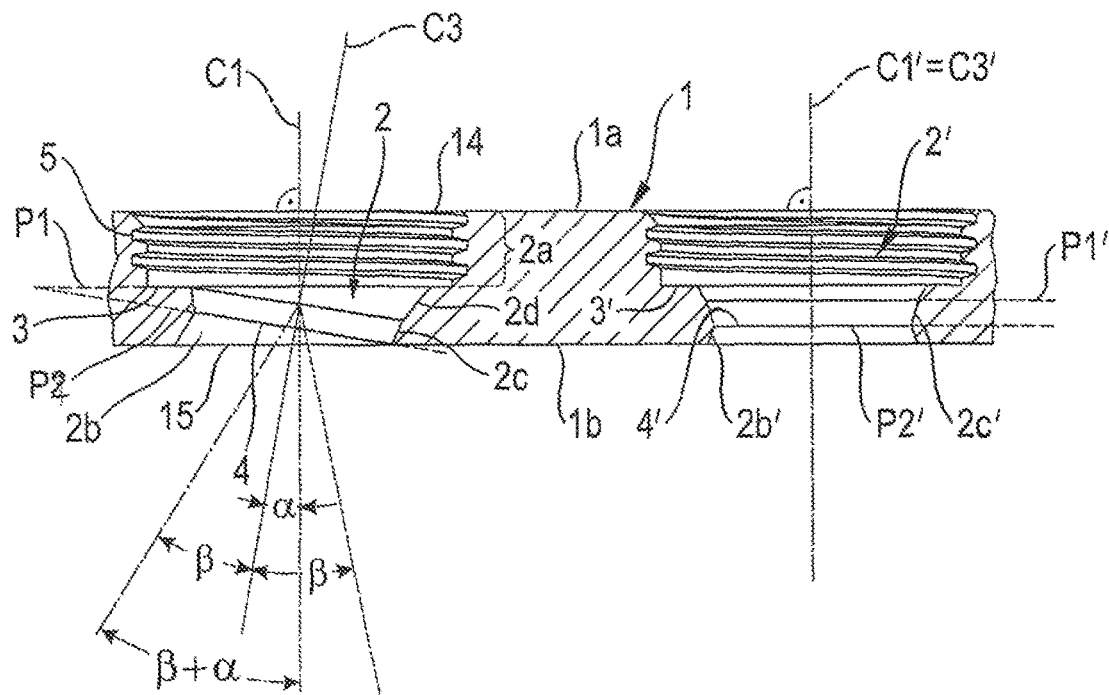
FIG. 1 shows a schematic cross-sectional view of a plate member of a bone plate assembly with a hole, according to a first embodiment.
Figure 2:
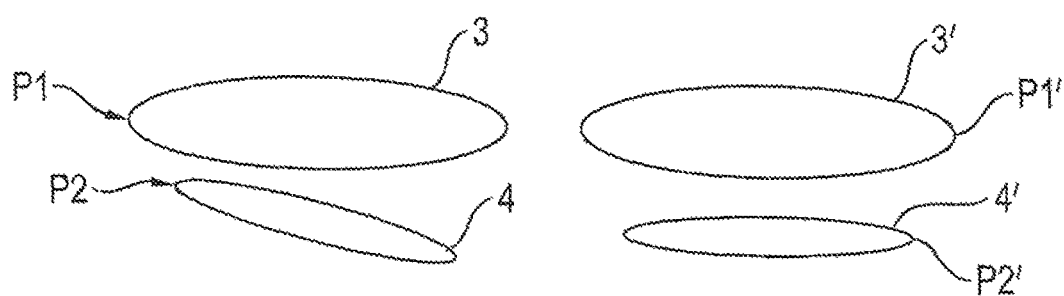
FIG. 2 shows a schematic view of the geometrical arrangement of the edges and planes defining the hole and the seat in FIG. 1.

A first embodiment of the bone plate assembly will now be described with reference to FIGS. 1 to 3. The bone plate assembly of the first embodiment is of the locking type, but can also be used as a non-locking plate. As can be seen in FIG. 1, the bone plate assembly includes a plate member 1 with a top side 1a, a bottom side 1b, the top side 1a and the bottom side 1b being substantially parallel to each other. A hole forming a passage 2 extends through the plate member 1 from the top side 1a to the bottom side 1b. The passage 2 is formed by three bores 2a, 2b, 2d and a seat portion 2c therebetween that is configured to receive the head of a bone anchor.

Figure 3:
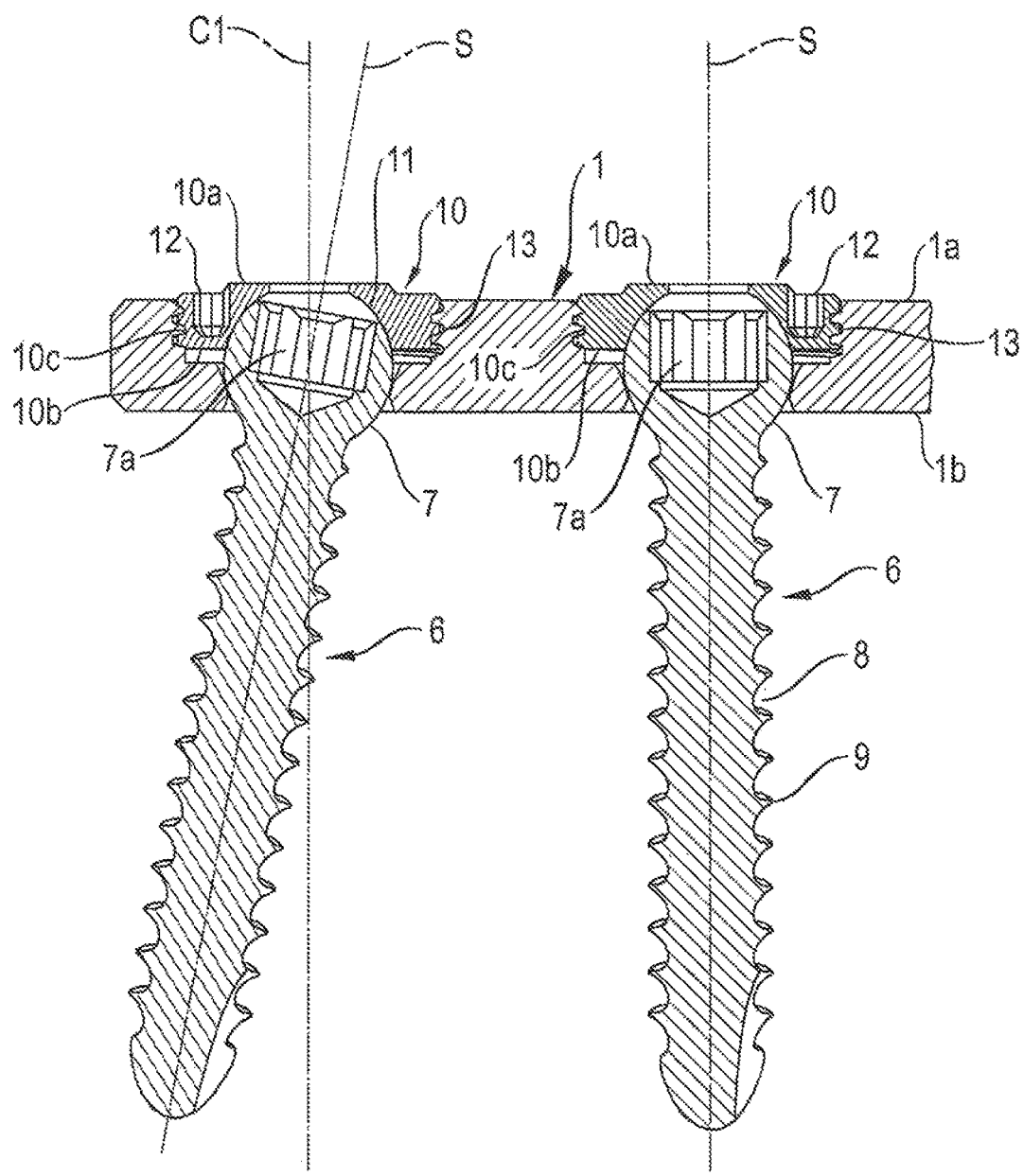
FIG. 3 shows a schematic cross-sectional sectional view of a bone plate assembly with a hole, a screw and a locking element according to the first embodiment.

Moreover, the assembly may comprise a bone anchor 6 with a head 7 and a shank 8 as can be seen in FIG. 3. In this embodiment, the bone anchor 6 is a bone screw having a head 7 with a spherically-shaped outer surface portion and a shank 8 with a bone thread 9 and a shank axis S. Typically, the head has an engagement structure 7a for a driver.

The first bore 2a of the passage 2 has a first end open towards the top side 1a of the plate member 1. At the top side 1a, the first bore defines an edge 14. The first bore 2a has a circular cross-section and an internal thread 5 for engagement with a locking element 10. The thread 5 may extend along the full axial length or along a portion of the length of the bore 2a. Further, the first bore 2a has a diameter that is larger than the largest diameter of the head 7 of the bone anchor 6. As can be seen in FIGS. 1 and 3, the first bore 2a substantially extends into the plate member 1 and ends around half of the thickness of the plate member 1 at its second end, where it forms an annular shoulder 3 within the passage 2. This annular shoulder 3 defines a first plane P1 as can be seen in FIGS. 1 and 2. The first bore 2a further comprises a bore axis or central axis C1, being also the central axis of the first plane P1. In the case that the top side 1a is parallel to the bottom side 1b, C1 is perpendicular to the top side 1a and the bottom side 1b of the plate member 1. This facilitates insertion and tightening of the locking element and the risk of cross-threading is minimized.

The second bore 2b is of conical shape and is open towards the bottom side 1b of plate member 1 and forms an inner surface. At the bottom side 1b, the second bore defines a circular or elliptical edge 15. The diameter of the second bore 2b is at least equal to the smallest diameter of the seat portion 2c with an increasing inner diameter towards the open end at the bottom side 1b of the plate member.

The seat portion 2c is formed by a hollow spherical segment-shaped portion that extends between the first bore 2a and the second bore 2b with decreasing inner diameter towards the second bore 2b. A central axis C3 of symmetry of the seat, in the following seat central axis C3, extends through the seat portion 2c. The seat central axis C3 of the seat portion is inclined with respect to the central axis C1 of the first bore 2a by an angle α. In this embodiment, angle α is approximately 10°. The seat central axis C3 intersects the central axis C1 at a position in the passage 2 that corresponds to the center point of the sphere defined by the spherical seat 2c. By the tapering design of the seat portion 2c, an inwardly extending annular edge 4 is formed between the seat portion 2c and the second bore 2b. The inwardly extending annular edge 4 defines the smallest diameter of the passage 2. Moreover, by the inwardly extending annular edge 4 a second plane P2 is defined with the seat central axis C3 being perpendicular thereto. By means of this, the second plane P2 is tilted relative to the first plane P1 and intersects the plane P1 at the angle α. The Zero-position (0°-position) of the bone anchor 6 is defined by the shank axis S being coaxial to the seat central axis C3.

The seat portion 2c partially extends to the bottom side 1b of the plate member 1. As can be seen in FIG. 1, the lowermost portion of the seat portion 2c at one side with respect to the central axis C3 of the seat portion 2c may be at the bottom side 1b of the plate member 1, while the opposite side is at a distance from the bottom side 1b. However, the lowermost portion of the seat portion 2c may also be located at some distance from the bottom side 1b. The uppermost portion of the seat portion 2c can be at the first plane P1 or can merge into the first bore 2a.

Additionally, the passage 2 includes a third bore 2d being arranged between the first bore 2a and the seat portion 2c and connecting them. As can be seen in FIG. 1, the diameter of the third bore 2d is equal to or more than the largest diameter of the head 4 of screw 3 and may be smaller than the diameter of the first bore 2a. The head 7 may be guided by the third bore 2d when it is inserted.

The maximum angle of inclination that the shank axis S can assume with respect to the seat central axis C3 may be defined by the diameter of the bore 2a relative to the largest outer diameter of the head 7 and the size and position of the engagement structure 7a for the driver. Additionally, the width of the second bore 2b may limit the maximum angle of inclination. The pivot angle of the bone anchor in the seat portion or the insertion angle of the bone anchor around the seat central axis C3 is an angle β resulting in a total range of motion of 2β.

Since the seat central axis C3 defines the Zero-position of the bone anchor 3 as mentioned above, the bone anchor 3 shown in the left side of FIG. 3 is angled at the angle α relative to the central axis C1 of plane P1 in its Zero-position. Hence, the shank axis S of the bone anchor is already angled with respect to the central axis C1 of the first bore 2a to the favored side in the Zero-position, which is 10° in this embodiment. Depending on the size of the first bore 2a and due to the design of the second bore 2b, it is possible to insert the bone anchor 6 into the bone at an angle of β relative to its Zero-position to the favored side. Consequently, the shank axis S of bone anchor 6 may be inclined to the favored side with a maximum angle that is the sum α+β which may be around 30° relative to the central axis C1 of the plane P1. As the motion cone is circular and thus symmetrical about the central axis C3, the angle of inclination to the side opposite from the favored side is reduced by the angle α starting from the bone anchor's Zero-position and thus is β−α in total. This however is not detrimental as the favored side is intended to be used for the angular position of the screw.

The position of the bone screw 6 relative to the plate 1 can be locked or stabilized by the above-mentioned locking element 10. In the embodiment shown, the locking element 10 is substantially cylindrical with a top side 10a, a bottom side 10b opposite to the top side 10a and an outer surface portion 10c therebetween. The diameter of the locking element 10 corresponds to the diameter of the first bore 2a. In an assembled state, the bottom side 10b is facing the head 7 of the bone anchor 6. As can be seen in FIG. 3, a first recess 11 is provided at the bottom side 10b for accommodating at least a portion of the head 7. The recess 11 has a spherically-shaped inner surface portion corresponding to the spherically-shaped outer surface portion of the head 7. At the top side 10a, at least one further recess 12 is provided for engagement with a driver. Moreover, the locking element 10 comprises an external thread 13 on its outer surface portion 10c. The external thread 13 is configured to interact with the internal thread 5 of the plate member 1. The height of the locking element 10 is smaller than the depth of the threaded bore 2a into the plate member 1. It may be desirable that the top side 10a of the locking element 10 is substantially flush with the top side 1 a of the plate member 1 when the head is locked by the locking element 10.

The plate member 1 may have a second passage 2' comprising a first bore 2a' with a central axis C1', a second bore 2b with a second bore axis C1' and a seat portion 2c' therebetween, having a central axis C3' and a third bore 2d' between the first bore 2a' and the seat portion 2c'. The first bore 2a' may be threaded. A shoulder 3' is formed between the first bore 2a' and the third bore 2d' within of the plate member 1, defining a plane P1' with a central axis C1' orthogonal thereto. Furthermore, the seat portion 2c' forms an inwardly extending annular edge 4' defining a second plane P2'. Contrary to passage 2 described before, the axes C1' and C3' extend coaxially through passage 2' and orthogonal to the top side 1a and the bottom side 1b of the plate member 1. Moreover, the planes P1' and P2' are extending in parallel to each other. Further, a bone anchor 6 and a locking element 10 may be provided, the locking element 10 for locking the bone anchor as explained above.

The plate member 1 may have several holes with passages of the type of the passage 2 and/or the passage 2'.

The elements of the bone plate assembly are made of a body compatible material, such as a body compatible metal, for example stainless steel or titanium or a body compatible metal alloy such as Ni—Ti alloys, for example Nitinol, or of a body compatible plastic material, for example medical grade PEEK or of a combination thereof. For example, the plate member and the bone anchors can be made of different materials.

Now, use of the bone plate assembly according to the first embodiment will be described. Once the necessary numbers and types of the bone anchors are determined, the plate member 1 is positioned at the fracture site. Then, the bone anchors are inserted into the first type passage 2 and/or second type passage 2' and inserted into the bone parts at the desired angle. The spherical seat allows placement of the head of the screw in the hole at this angle. The bone screw 6 inserted into the first passage type 2 can assume a 10° larger angle of inclination to the favored side compared to the bone anchor inserted into the second passage type 2'.

To further stabilize the connection between the bone anchor and the plate member the locking element 10 can optionally be used which is inserted into the first bore 2a, 2a and tightened so that it locks the head 7. If desired, the different locking elements can be applied to different bone anchors in order to provide for full locking, frictional locking or no locking where the locking member only prevents pull-out of the screw as described above. It may be noted that locking elements without thread but with another locking structure may be used to lock the head 7.

Alternatively, the bone plate can be used without a locking element as a non-locking plate.

In a second embodiment of a so-called non-locking plate, the first bore 2a, 2a may be provided threadless.

Figure 4:
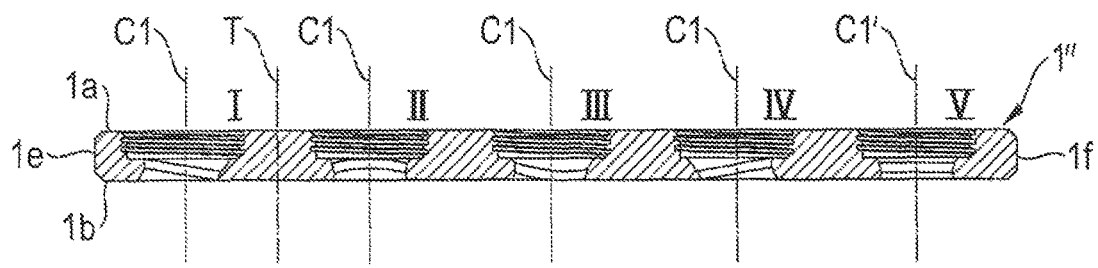
FIG. 4 shows a schematic cross-sectional view of a plate member of a bone plate assembly with several holes according to an embodiment.

A third embodiment will be explained with reference to FIGS. 4 to 6. In this embodiment, the bone plate assembly comprises an elongate plate member 1" with a planar upper side 1a, a planar bottom side 1b being parallel to the planar upper side 1a, a first and a second side wall 1c and 1d and a first and a second curved side wall 1e and 1f. Further, the plate member 1" comprises a central longitudinal axis L and a vertical axis T being parallel to each of the central axes C1 and C1' respectively of the first bores 2a and 2a respectively, wherein the vertical axis T extends orthogonally from the top side 1a and the bottom side 1b of the elongate plate member 1. Five holes I to V extend through the elongate plate member 1" on the longitudinal axis L, wherein the first four holes I to IV (from left to right) are formed by passages according to the first embodiment. Contrary, the fifth hole V comprises solely bores with one single common central axis.

Figure 5:
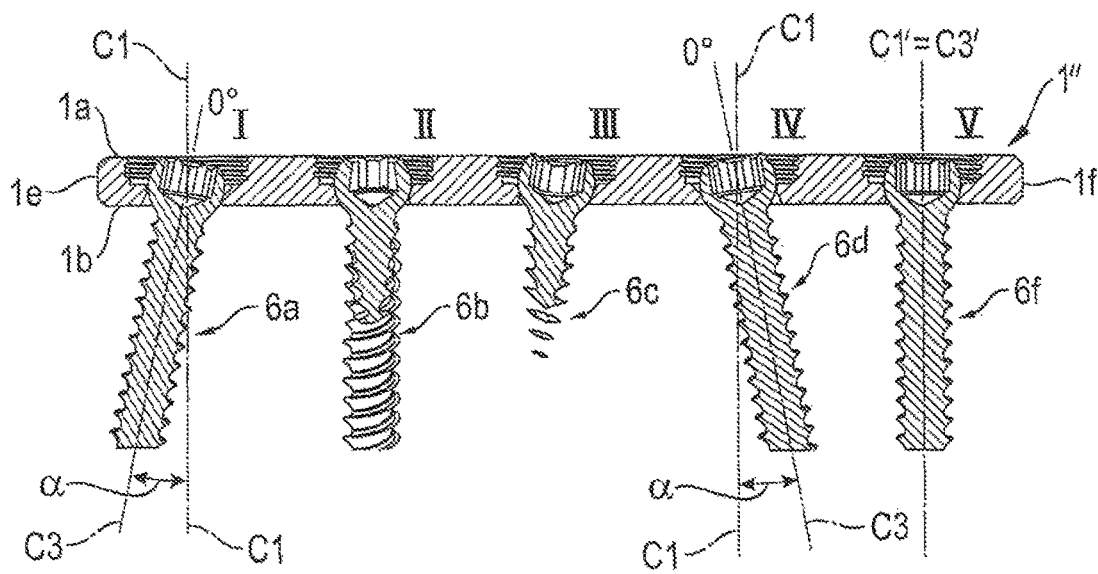
FIG. 5 shows a schematic cross-sectional view of a bone plate assembly including the plate member with several holes according to FIG. 4, along with several screws and locking elements.
Figure 6:
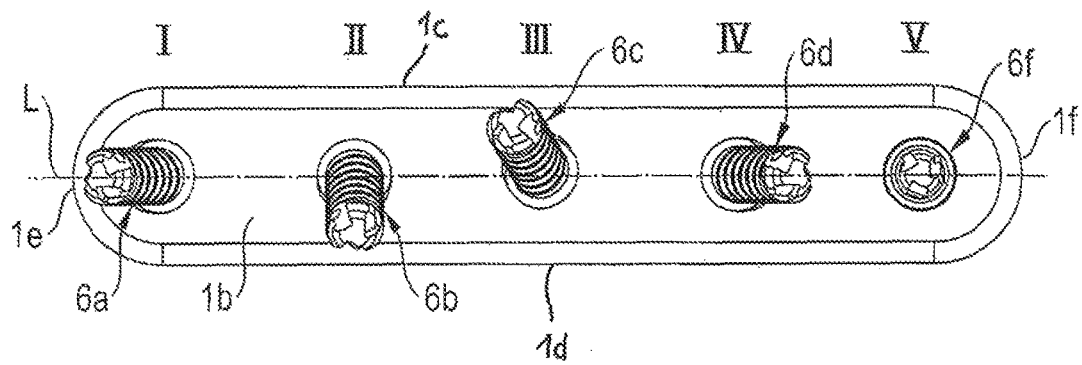
FIG. 6 shows a bottom view of the bone plate assembly according to FIG. 5.

As can best be seen in FIGS. 5 and 6, the orientation of the seat portions 2c is such that the Zero-positions of the first four screws 6a to 6d differ from the Zero-position of the fifth screw 6f. The Zero-position of the first four screws are tilted relative to Zero-position of the fifth screw by an angle, for example by approximately 10°, each in another direction of the four directions relative thereto. This may be useful in specific anatomical conditions. The number and the angle of the Zero-position may be adapted to such a specific condition.

Figure 7:
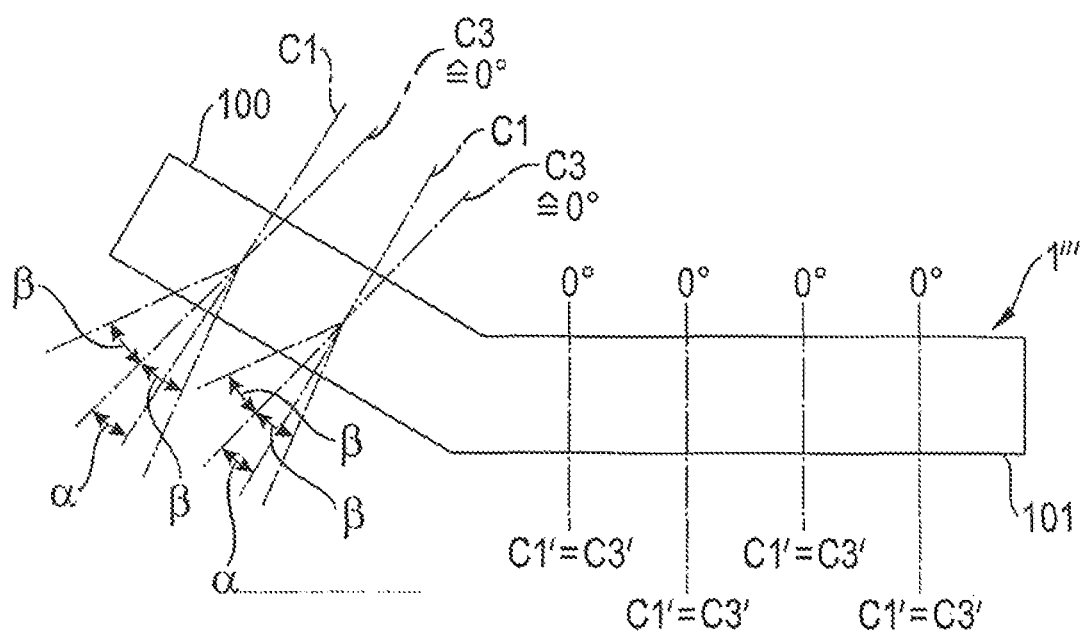
FIG. 7 shows a sectional view of an angled bone plate with schematic motion cones according to an embodiment.

A fourth embodiment will now be described with reference to FIG. 7. This embodiment comprises a bone plate assembly with an upwardly angled elongate plate member 1'''. The bone plate member includes an upwardly angled bone plate portion 100 as well as a planar bone plate portion 101. Two passages extend through the angled bone plate portion 100 and four through the planar bone plate portion 101. Furthermore, the corresponding Zero-positions and the corresponding motion cones of a bone anchor are indicated. In this embodiment, the first and the second hole in the angled bone plate portion 100 have a design according to the first or the second embodiment allowing an increased insertion angle of a bone anchor in the direction of the inclination of the bone plate member 1'''.

Further embodiments are possible. For example, the first bore 2a may be conically-shaped tapering towards the lower side with a smallest diameter being equal to the largest diameter of a screw head. In a still further embodiment, the second bore 2b may be cylindrically-shaped with such a size that it limits the angle β. In a specific embodiment β may be zero so that the shank axis S can assume only the angle α with respect to the central axis C1 of the first bore 2a.

Furthermore, the seat may be conically-shaped or otherwise shaped, such that the seat and the head of the bone anchor form a ball- and socket-joint.

P1 may be tilted with respect to the top side 1a and/or the bottom side 1b. This may be the case if the top side 1a and the bottom side 1b are not substantially parallel or have an irregular structure.

Moreover, the bone plate may have additionally or instead an alternative hole configured to receive an insert, wherein the insert comprises the angled seat portion 2c as described above.

It should be clear from the above that the number, the design (for example in terms of the orientation and the extent of the enlarged angle of inclination) as well as the arrangement of the different holes can be varied according to the anatomical situation. For example, the holes may be offset from the central longitudinal axis L. The shape of the bone plate may be elongate, rectangular or otherwise shaped and/or curved and may have different sizes. Moreover, different embodiments can be combined among each other to provide a specific plate member needed for a specific application.

Instead of the bone screw with a threaded shank any other bone anchor having a shank for anchoring in the bone, such as for example a bone nail, with or without barbs, can be used. The shank may also be cannulated and may have openings in the wall to allow introduction of bone cement or other substances.

What is claimed is:

1. A bone plate assembly comprising:
a plate member having a top side and a bottom side,
   at least one passage extending from the top side to the bottom side;
   wherein the at least one passage includes a first bore with a first end open towards the top side and a second end;
   a seat portion configured to receive and circumferentially support and contact a head of a bone anchor,
   wherein the first bore comprises a first central axis and the seat portion comprises a second central axis, wherein the first central axis and the second central axis intersect each other within the passage, and wherein a surface defining the seat portion has a circular shape in a cross-sectional plane transverse to the second central axis;
   a second bore open towards the bottom side; and
   a third bore provided between the first bore and the seat portion and open towards the first bore and the seat portion, wherein the third bore has a diameter that is at least equal to the largest diameter of the seat portion and smaller than the smallest diameter of the first bore, and wherein the third bore tapers in diameter along the second central axis from the first bore to the seat portion.

2. The bone plate assembly according to claim 1, wherein the second end of the first bore defines a first plane and wherein an inwardly extending lower edge of the seat portion that faces towards the bottom side defines a second plane, and wherein the first plane and the second plane intersect each other at an angle α.

3. The bone plate assembly according to claim 2, wherein the angle α is approximately 1 to 20°.

4. The bone plate assembly according to claim 3, wherein the angle α is about 10°.

5. The bone plate assembly according to claim 1, wherein the seat portion is configured to receive a head of a bone anchor at different angular orientations of the head.

6. The bone plate assembly according to claim 1, wherein the second bore has a diameter that is at least equal to the smallest diameter of the seat portion.

7. The bone plate assembly according to claim 1, wherein the inner diameter of the second bore increases towards the open end at the bottom side of the plate member.

8. The bone plate assembly according to claim 1, wherein the first bore comprises an internal thread.

9. The bone plate assembly according to claim 8, further comprising a locking element configured to be received in the first bore and maintain a position of a bone anchor in the seat portion, the locking element comprising an external thread configured to engage the internal thread of the first bore.

10. The bone plate assembly according to claim 1, wherein the first bore is substantially cylindrical.

11. The bone plate assembly according to claim 1, wherein the first central axis is substantially orthogonal to the top side and/or to the bottom side of the plate member.

12. The bone plate assembly according to claim 1, wherein the seat portion partially extends to the bottom side of the plate member.

13. The bone plate assembly according to claim 1, wherein the lowermost portion of the seat portion at one side is at the bottom side or at a distance from the bottom side.

14. The bone plate assembly according to claim 1, wherein the seat portion has a spherically-shaped surface portion.

15. The bone plate assembly according to claim 1, further comprising a bone anchor including a head receivable in the seat portion, and a shank with a shank axis, and
   wherein, when the head is received in the seat portion, the second central axis defines a zero-position for said bone anchor, in which the shank axis is coaxial to the second central axis.

16. The bone plate assembly according to claim 15, wherein the first bore has a diameter that is at least equal to the largest diameter of the head of the bone anchor.

17. The bone plate assembly according to claim 15, wherein the bone anchor is configured to pivot in the seat portion symmetrically with an angle of 1 to 30° relative to the zero-position.

18. The bone plate assembly according to claim 17, wherein the bone anchor is configured to pivot in the seat portion symmetrically with an angle of about 20° relative to the zero-position.

19. The bone plate assembly according to claim 15, wherein the head has a spherically-shaped outer surface portion.

20. The bone plate assembly according to claim 1, further comprising a locking element configured to be received in the first bore and maintain a position of a bone anchor in the seat portion.

21. The bone plate assembly according to claim 20, wherein the locking element is substantially cylindrical with a bottom side configured to face a head of a bone anchor, a top side opposite to the bottom side of the locking element; and wherein the locking element has a first recess at the bottom side of the locking element for accommodating at least a portion of the head and a second recess at the top side of the locking element for engagement with a driver.

22. The bone plate assembly according to claim 1, wherein at least a portion of the top side of the plate member and a portion of the bottom side of the plate member that comprise the passage are substantially parallel to each other.

23. The bone plate assembly according to claim 1, wherein the plate member comprises at least one further passage.

24. The bone plate assembly according to claim 1, wherein the plate member comprises a first portion and a second portion that extends at an angle with respect to the first portion.

25. The bone plate assembly according to claim 1, wherein the first central axis and the second central axis intersect each other at a point corresponding to the center point of the seat portion.

26. The bone plate assembly according to claim 1, wherein the first central axis and the second central axis intersect at an angle.

27. The bone plate assembly according to claim 1, wherein the third bore conically tapers about the second central axis.

28. The bone plate assembly according to claim 1, further comprising:
the bone anchor including the head, the head having a spherical outer surface portion; and
a locking element configured to be engagingly received in the first bore,
wherein when the spherical outer surface portion of the head is received in the seat portion and the locking element is engagingly received in the first bore, the locking element engages the spherical outer surface portion of the head of the bone anchor to maintain a position of the bone anchor in the seat portion.

29. A bone plate assembly comprising:
a plate member having a top side and a bottom side,
at least one passage extending from the top side to the bottom side;
wherein the at least one passage includes a first bore with a first end open towards the top side and a second end, the second end forming an annular edge within the passage, the annular edge defining a first plane, wherein the first bore defines a first edge at the top side,
a second bore open towards the bottom side, wherein the second bore defines a second edge at the bottom side, and
a seat portion configured to receive and circumferentially support and contact a head of a bone anchor, wherein a surface defining the seat portion has a circular shape in a cross-sectional plane transverse to a central axis of the seat portion, and
a third bore provided between the first bore and the seat portion and open towards the first bore and the seat portion, wherein the third bore has a diameter that is at least equal to the largest diameter of the seat portion and smaller than the smallest diameter of the first bore, and wherein the third bore tapers in diameter along the second central axis from the first bore to the seat portion,
wherein the seat portion has a decreasing width towards the bottom side forming an inwardly extending lower edge between the seat portion and the second bore, the inwardly extending lower edge defining a second plane,
wherein the first plane and the second plane intersect each other at an angle.

30. The bone plate assembly of claim 29, wherein the first edge of the first bore at the top side is substantially parallel to the second edge of the second bore at the bottom side.

31. The bone plate assembly according to claim 29, further comprising:
the bone anchor including the head, the head having a spherical outer surface portion; and
a locking element configured to be engagingly received in the first bore,
wherein when the spherical outer surface portion of the head is received in the seat portion and the locking element is engagingly received in the first bore, the locking element engages the spherical outer surface portion of the head of the bone anchor to maintain a position of the bone anchor in the seat portion.

32. A bone plate assembly comprising:
a bone anchor including a head;
a plate member having a top side and a bottom side,
at least one passage extending from the top side to the bottom side,
wherein the at least one passage includes a first bore with a first end open towards the top side and a second end,
a seat portion configured to receive and circumferentially support and contact the head of the bone anchor,
wherein the first bore comprises a first central axis and the seat portion comprises a second central axis, and wherein the first central axis and the second central axis intersect each other within the passage,
a second bore open towards the bottom side, and
a third bore provided between the first bore and the seat portion and open towards the first bore and the seat portion, wherein the third bore has a diameter that is larger than a largest diameter of the seat portion and smaller than the smallest diameter of the first bore; and
a locking element configured to be received in the first bore, the locking element comprising a bottom side configured to face the head of the bone anchor and a recess at the bottom side of the locking element to accommodate at least a portion of the head to engage the head of the bone anchor to maintain a position of the bone anchor in the seat portion.

33. The bone plate assembly according to claim 32, wherein the first bore comprises an internal thread, and wherein the locking element comprises an external thread configured to engage the internal thread of the first bore.

34. The bone plate assembly according to claim 32, wherein:
the head of the bone anchor has a spherical outer surface portion,
wherein when the spherical outer surface portion of the head is received in the seat portion and the locking element is engagingly received in the first bore, the recess of the locking element receives the spherical outer surface portion of the head of the bone anchor to maintain a position of the bone anchor in the seat portion.

35. The bone plate assembly according to claim 32, wherein the third bore tapers in diameter along the second central axis from the first bore to the seat portion.

36. A bone plate assembly comprising:
a plate member having a top side and a bottom side,
at least one passage extending from the top side to the bottom side,
wherein the at least one passage includes a first bore with a first end open towards the top side and a second end,
a seat portion,
wherein the first bore comprises a first central axis and the seat portion comprises a second central axis, and wherein the first central axis and the second central axis angularly intersect each other within the passage,
a second bore open towards the bottom side;
a bone anchor including a head receivable into contact with an entire circumference of the seat portion, and a shank having a shank axis; and
a unitary locking element configured to be received in the first bore and directly engage the head of the bone anchor to maintain a position of the bone anchor in the seat portion;
wherein, when the head is circumferentially received in the seat portion, the second central axis defines a zero-position for the bone anchor, in which the shank axis is coaxial to the second central axis.

37. The bone plate assembly according to claim 36, wherein:
the head of the bone anchor has a spherical outer surface portion, and the spherical outer surface portion is received in the seat portion and engaged by the locking element.

38. A bone plate assembly comprising:
a bone anchor having a head with a substantially spherical outer surface and having a bone-engaging shaft;
a locking element having an upper surface and a lower concave recess configured to receive the substantially spherical outer surface of the head of the bone anchor; and
a plate member having a top side and a bottom side,
at least one passage extending from the top side to the bottom side,
wherein the at least one passage includes a first bore with a first end open towards the top side and a second end, the first end configured to engagingly receive the locking element, and
a seat portion configured to receive and circumferentially support and contact the head of the bone anchor,
wherein the first bore comprises a first central axis and the seat portion comprises a second central axis, the first central axis and the second central axis angularly intersecting each other within the passage, and
wherein a surface defining the seat portion has a circular shape in a cross-sectional plane transverse to the second central axis.

39. The bone plate assembly according to claim 38, wherein when the bone anchor is received in the seat portion and the locking element is engagingly received in the first end of the at least one passage to lock an angular position of the bone anchor relative to the seat portion, the head of the bone anchor is retained below the upper surface of the locking element.

\* \* \* \* \*